US00PP21224P2

(12) United States Plant Patent

Grosser et al.

(10) Patent No.: US PP21,224 P2

(45) Date of Patent: Aug. 24, 2010

(54) SWEET ORANGE TREE NAMED 'N7-3'

(50) Latin Name: ***Citrus sinensis* L. Osbeck**
Varietal Denomination: N7-3

(75) Inventors: Jude W. Grosser, Winter Haven, FL (US); Frederick G. Gmitter, Jr., Lakeland, FL (US); William S. Castle, Lake Alfred, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/454,988

(22) Filed: May 27, 2009

(51) Int. Cl.
*A01H 5/00* (2006.01)

(52) U.S. Cl. ..... Plt./202

(58) Field of Classification Search ..... Plt./202
See application file for complete search history.

(56) References Cited

OTHER PUBLICATIONS

Grosser, et al. (2007) Somaclonal Variation in Sweet Orange: Practical Applications for Variety Improvement and Possible Causes in: *Citrus* Genetics, Breeding and Biotechnology (ed. I.A. Khan). CAB International. pp. 219-233.

Larkin, et al. (1981) Somaclonal Variation—a Novel Source of Variability from Cell Cultures for Plant Improvement. Theor. Appl. Genet. 60, pp. 197-214.

*Primary Examiner*—Susan B McCormick Ewoldt
(74) *Attorney, Agent, or Firm*—Jondle & Associates, P.C.

(57) ABSTRACT

A new Valencia-derived sweet orange tree particularly distinguished by trees that bear virtually seedless (an occasional seed can be found) 'Valencia' type sweet orange fruit, fruit that ripens slightly later than standard 'Valencia' trees, good fruit quality which holds into June and fruit having good juice quality when no other commercial *citrus* is available in Florida, is disclosed.

2 Drawing Sheets

Genus and species: *Citrus sinensis* L. Osbeck.
Variety denomination: 'N7-3'.

BACKGROUND OF THE NEW PLANT

The invention relates to a new and distinct variety of sweet orange tree, *Citrus sinensis* L. Osbeck, named 'N7-3'. 'N7-3' is a moderately vigorous tree that produces standard 'Valencia' type sweet orange fruit but unlike standard 'Valencia' clones, the fruit of 'N7-3' is virtually seedless (an occasional seed can be found) and exhibits a fruit maturation date later (2 to 8 weeks) than standard 'Valencia' trees. In Florida, the fruit quality of 'N7-3' can generally be harvested from mid-March through June, depending on environmental conditions. Juice quality from fruit of 'N7-3' is equivalent to that of standard 'Valencia', the highest quality juice from oranges currently available. 'N7-3' is a dual-use, late-season cultivar that can be used for fresh market or processing.

'N7-3' originated as a 'Valencia' somaclonal tree regenerated from protoplasts isolated from an embryogenic suspension culture of standard 'Valencia' (*Citrus sinensis* L. Osbeck) in 1989. For the methodology, please see Grosser, J. W. and F. G. J. Gmitter (1990). Protoplast fusion and *citrus* improvement. Pp. 339-374. In: Janick, J. (Ed.). *Plant Breeding Reviews*. Timber Press, Inc., Portland, Oreg., USA. The original tree was grafted to 'Swingle' citrumelo rootstock and was planted in Lake Alfred, Fla. in 1991. 'N7-3' is a true seedless 'Valencia' sweet orange with an altered maturity date that allows for an extended harvest beyond the time when any quality commercial *citrus* is available in Florida.

'N7-3' has been subsequently asexually propagated by conventional bud-grafting onto 'Swingle' and 'Carrizo' rootstocks. The present invention has been found to retain its distinctive characteristics through successive asexual propagations.

Plant Breeder's Rights for this cultivar have not been applied for. 'N7-3' has not been made publicly available or sold more than one year prior to the filing of this application.

SUMMARY OF THE INVENTION

'N7-3' is a new and distinct variety of sweet orange tree which bears seedless fruit that ripens around mid-March and holds quality through June during most years. 'N7-3' trees usually bloom between early to late March in central Florida, depending on environmental conditions. 'N7-3' trees have an upright plant habit and of moderate vigor, typical of 'Valencia' sweet orange trees.

'N7-3' trees bear fruit that is typical of 'Valencia' trees but 'N7-3' ripens slightly later (usually mid-March) and hold good fruit quality well into June in Florida. Juice quality of 'N7-3' fruit is typical of 'Valencia' fruit in sugar and acid content, color and flavor. 'N7-3' fruit are juicy, difficult to peel and seedless, with an occasional seed, unlike standard 'Valencia' fruit, which averages 3.9 seeds per fruit. Replicated trials (both second generation and top-worked third generation trees), to determine yield were destroyed by the Florida state-run canker eradication program. Based on observations, 'N7-3' appears to yield slightly less fruit than standard 'Valencia' trees, but is adequate for commercial harvesting.

The following are the most outstanding and distinguishing characteristics of this new cultivar when grown under normal horticultural practices in Florida.

1. Trees that bear seedless 'Valencia' type sweet orange fruit;
2. Fruit that ripens slightly later than standard 'Valencia' trees;
3. Good fruit quality which holds into June; and 4. Fruit having good juice quality when no other commercial *citrus* is available in Florida.

DESCRIPTION OF THE PHOTOGRAPHS

This new sweet orange plant is illustrated by the accompanying photographs which show the plant's form, foliage and fruit. The colors shown are as true as can be reasonably obtained by conventional photographic procedures. The tree photographs were taken in January 2009, and the photo of the fruit was taken in March 2008.

DESCRIPTION OF THE NEW CULTIVAR

Figure 1:
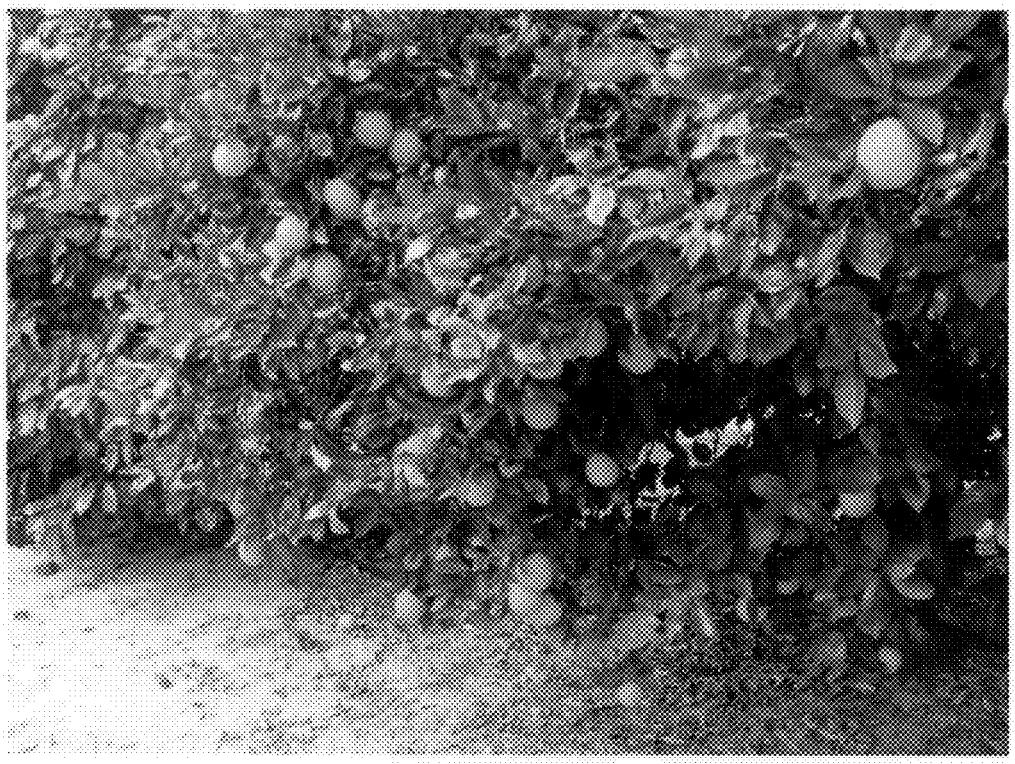
FIG. 1 shows a section of the original 'N7-3' tree on 'Swingle' rootstock taken prior to harvest in 2009.
Figure 2:
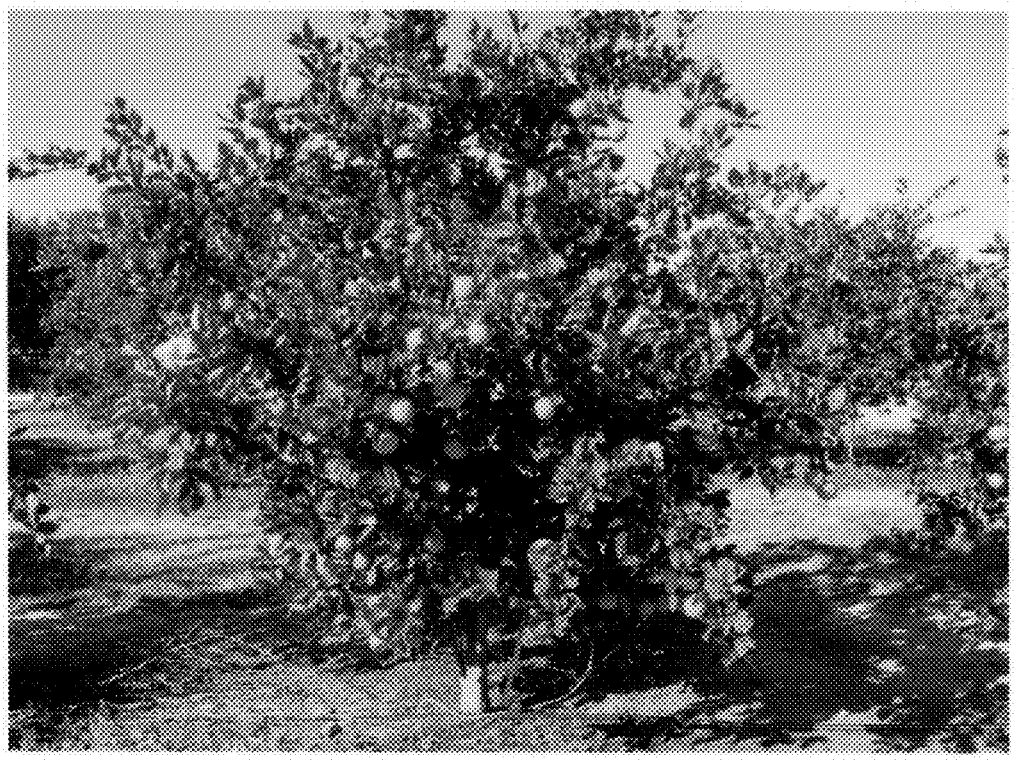
FIG. 2 shows fruit cropping on a 5-year old 'N7-3' tree on 'Carrizo' citrange rootstock.
Figure 3:
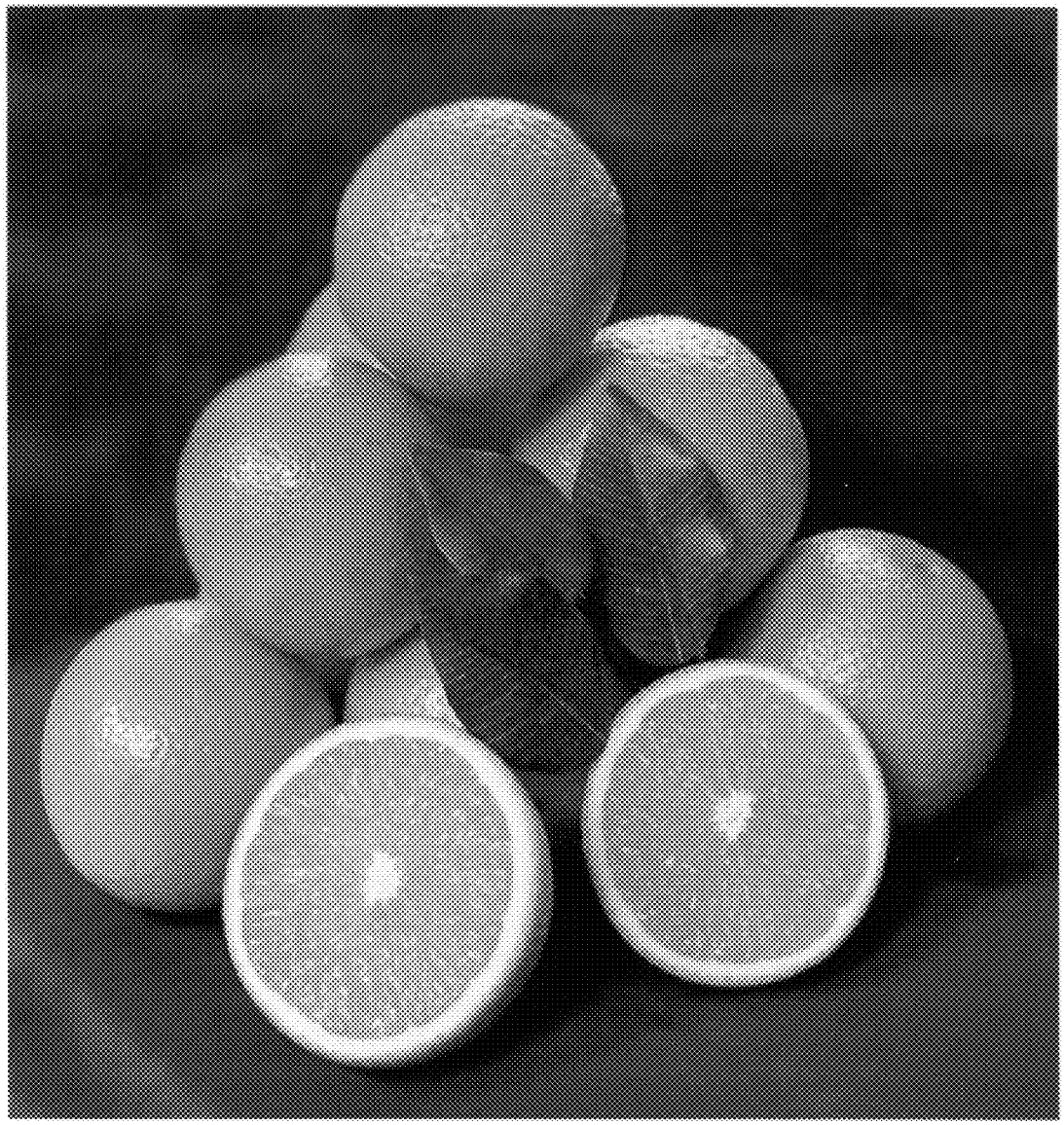
FIG. 3 shows a close-up of the mature fruit, a cross-sectional view of the fruit and a longitudinal sectional view of the fruit.

The following detailed description defines the characteristics of 'N7-3'. The present botanical description is that of the variety grown at the University of Florida Citrus Research and Education Center in Lake Alfred, Fla. in 2007 and 2008 on 'Swingle' citrumelo rootstock (original tree, 18 years old) or 'Carrizo' citrange rootstock (second generation trees, 5 years old). The colors (except those in common terms) are described from RHS Colour Chart published by The Royal Horticultural Society in London, in association with the Flower Council of Holland (2001).

DETAILED BOTANICAL DESCRIPTION

Classification:

*Botanical.*—*Citrus sinensis* L. Osbeck.

*Common name.*—Sweet orange.

*Parentage.*—Somaclonal tree regenerated from protoplasts isolated from an embryogenic suspension of tissue culture of standard 'Valencia' (unpatented).

Tree:

*Ploidy.*—Diploid.

*Form.*—Obloid, typical of 'Valencia' sweet orange.

*Vigor.*—Moderate; typical of 'Valencia' sweet orange.

*Size.*—Typical of 'Valencia' type trees; depends on the rootstock used; height of mature tree on 'Swingle' citrumelo rootstock is approximately 4.4 m.

*Trunk diameter (on 'Swingle' citrumelo rootstock).*—18.0 cm.

*Bark color.*—Between RHS 199 (Greyed-brown) to RHS N199A (Greyed-brown).

*Density.*—Typical of 'Valencia' sweet orange.

*Thorn length.*—1.5 cm±0.6 cm.

*Thorn color.*—Between RHS 199 (Greyed-brown) to RHS N199A (Greyed-brown), depending on the age of the bark.

*Thorn shape.*—Straight.

Leaves:

*Type and shape.*—Simple and elliptical.

*Apex.*—Acuminate.

*Base.*—Obtuse.

*Margin.*—Entire margin is moderately articulate.

*Length.*—7.67 cm.

*Width.*—4.61 cm.

*Adaxial color.*—RHS 137A (Green).

*Abaxial color.*—RHS 144A (Yellow-green).

*Texture.*—Smooth.

*Petiole.*—Appearance and attachment: Articulate and brevipetiolate. Length: 1.32 cm. Width: 0.32 cm. Color: RHS 137A (Green).

Flowers:

*Blooming period in central Florida.*—Early to late March.

*Petals.*—Quantity (per flower): 3.7±0.5 to 4.6±0.5. Length: 1.35 cm±0.20 cm to 1.78 cm±0.26 cm. Width: 0.6 cm±0.1 cm to 0.66 cm±0.12 cm. Color: RHS 155D (White).

Fruit:

*Time of maturity.*—About mid-March in central Florida.

*Shape.*—Spheroid, with some that are slightly oval in shape.

*Apex.*—Rounded.

*Base.*—Convex.

*Fruit (flesh) color.*—RHS N25C (Orange).

*Height.*—7.5 cm±3.6 cm.

*Width.*—7.3 cm±4.2 cm.

*Fruit height to width ratio.*—Approximately 1.02.

*Individual fruit weight.*—208 g±31 g.

*Rind.*—Texture: Pitted. Color: RHS N25C (Orange). Thickness: 0.38 cm±0.08 cm to 0.47 cm±0.09 cm.

*Adherence of mesocarp to endocarp.*—Strong.

*Attachment to stalk (strength).*—Medium.

*Albedo color.*—RHS 10C (Yellow).

*Albedo thickness.*—0.2 cm to 0.5 cm.

*Segments.*—Quantity (per fruit): 10.4±0.8 to 10.4±0.87. Wall thickness: Thin. Vesicle length: 1.07 cm±0.13 cm. Vesicle width: 2.3 cm±0.07 cm.

*Naval.*—Absent.

Seeds:

*Quantity per fruit.*—The original 'N7-3' tree yielded approximately 0.17±0.42 seeds per fruit; the second generation 'N7-3' trees yielded approximately 0.05 seeds per fruit while standard 'Valencia' fruit averages approximately 3.9 seeds per fruit.

*Surface appearance.*—Wrinkled.

*Seed coat color.*—RHS 158B (Yellow-white).

*Inner seed coat color.*—RHS 165C (Greyed-orange).

*Outer seed coat color.*—RHS 161D (Greyed-yellow).

*Chalazal end color.*—RHS 165A (Greyed-orange).

*Cotyledon color.*—RHS 157D (Green-white).

Reproductive organs:

*Anther length.*—Shorter than petals.

*Anther color.*—RHS 15B (Yellow-orange).

*Stamen quantity.*—23.7±2.9.

*Stamens per petal.*—Approximately 5.1.

*Filaments.*—Are fused.

Juice Data: 'N7-3' has a later maturity date than standard 'Valencia' trees, which is the latest available commercial variety in Florida. Juice data from 'N7-3' fruit shows that 'N7-3' holds good fruit quality into June by maintaining a higher fruit acid level that keeps a brix/acid ratio in the preferred range of 15 to 18 (minimum legal ratio is 12). Additionally, the juice percentage obtained from 'N7-3' fruit averages about 49% to 55.5%, increasing with the age of the tree.

COMPARISON WITH PARENTAL AND KNOWN CULTIVARS

'N7-3' differs from the commercial comparison variety 'Alvarina' (U.S. Plant Pat. No. 19,575) in that 'N7-3' has smaller leaves (7.67 cm in length and 4.61 cm in width) with acuminate apices, while 'Alvarina' has larger leaves (10.0 cm to 12.0 cm in length and 8.0 cm to 10.0 cm in width) with generally cuspidate apices. Additionally, when compared to 'Alvarina', the fruit and juice of 'N7-3' have a richer (deeper) orange color.

Table 1 shows comparative data of juice characteristics from 'N7-3' as compared to the parental variety 'Valencia' (unpatented).

TABLE 1

Juice Data from 'N7-3' as compared to 'Valencia' (Location: CREC North-40 Grove, Lake Alfred, Florida, 'Swingle' citrumelo rootstock)

| Date | Variety | Brix | Acid | Ratio | Lb solids | Color |
|---|---|---|---|---|---|---|
| May 14, | 'N7-3' | 12.18 | 0.70 | 17.40 | 6.35 | 37.9 |
| 1998 | 'Valencia' | 13.44 | 0.57 | 23.58 | 7.21 | 37.7 |
| Feb. 19, | 'N7-3' | 11.43 | 1.16 | 9.85 | 6.54 | 36.9 |
| 1999 | 'Valencia' | 10.93 | 0.83 | 13.17 | 5.44 | 36.8 |
| Jun. 19, | 'N7-3' | 11.57 | 0.62 | 18.7 | 5.25 | 39.1 |
| 2000 | 'Valencia' | 12.81 | 0.51 | 25.1 | 6.44 | 39.0 |
| May 15, | 'N7-3' | 10.82 | 0.79 | 13.7 | 4.98 | 37.9 |
| 2001 | 'Valencia' | 10.86 | 0.58 | 18.7 | 6.43 | 39.3 |
| Mar. 14, | 'N7-3' | 11.72 | 0.91 | 12.88 | 6.32 | 37.8 |
| 2003 | 'Valencia' | 12.46 | 0.90 | 13.84 | 6.54 | 38.2 |

TABLE 1-continued

Juice Data from 'N7-3' as compared to 'Valencia' (Location: CREC North-40 Grove, Lake Alfred, Florida, 'Swingle' citrumelo rootstock)

| Date | Variety | Brix | Acid | Ratio | Lb solids | Color |
|---|---|---|---|---|---|---|
| Feb. 28, | 'N7-3' | 12.30 | 1.33 | 9.25 | 6.11 | n.d. |
| 2006 | 'Valencia' | 12.69 | 1.15 | 11.03 | 6.67 | n.d. |
| Apr. 10, | N7-3' | 11.86 | 0.80 | 14.83 | 6.00 | 39.2 |
| 2007 | 'Valencia' | 12.96 | 0.75 | 17.28 | 6.71 | 39.9 |

*Juice quality data was obtained from the UF/CREC State Test House
Brix: is the percent of sucrose determined with a hydrometer.
Acid: is the percent of citric acid determined by standard titration.
Ratio is Brix/Acid
Lb solids was calculated as pounds of soluble sugars per 90 lb box of fruit.
FDA legal juice color was measured used a Gretag Macbeth Color-Eye 3100 spectrophotometer. The computer software that is used with this machine is PorPalette 5.2.1 Quality Control 2001.
n.d = not determined Resistance to insects, disease or pests: Typical of standard 'Valencia' sweet orange trees.

We claim:

1. A new and distinct cultivar of sweet orange tree as shown and described herein.

* * * * *